United States Patent
Berg et al.

[11] Patent Number: 5,951,495
[45] Date of Patent: Sep. 14, 1999

[54] CATHETER HAVING AN ADHESIVE BRAID WIRE CONSTRAINT AND METHOD OF MANUFACTURE

[75] Inventors: Todd A. Berg, Lino Lakes; Jason A. Galdonik, Bloomington, both of Minn.

[73] Assignee: SciMed Life Systems, Inc., Maple Grove, Minn.

[21] Appl. No.: 08/800,926

[22] Filed: Feb. 13, 1997

Related U.S. Application Data

[63] Continuation-in-part of application No. 08/441,260, Aug. 15, 1995, Pat. No. 5,603,705, which is a continuation of application No. 08/171,925, Dec. 22, 1993, abandoned.

[51] Int. Cl.$^6$ .................................................. A61B 5/00
[52] U.S. Cl. ........................... 600/585; 600/435; 604/282
[58] Field of Search .................................. 600/585, 435; 604/280, 282, 283

[56] References Cited

U.S. PATENT DOCUMENTS

| | | | |
|---|---|---|---|
| 3,485,234 | 12/1969 | Stevens | 128/2 |
| 3,612,058 | 10/1971 | Ackerman | 128/348 |
| 4,210,478 | 7/1980 | Shoney | 156/242 |
| 4,419,095 | 12/1983 | Nebergall et al. | 604/96 |
| 4,516,970 | 5/1985 | Kaufman et al. | 604/270 |
| 4,516,972 | 5/1985 | Samson | 604/282 |
| 4,531,943 | 7/1985 | Van Tassel et al. | 604/280 |
| 4,588,399 | 5/1986 | Nebergall et al. | 604/280 |
| 4,705,511 | 11/1987 | Kocak | 604/282 |
| 4,817,613 | 4/1989 | Jaraczewski et al. | 128/658 |
| 4,842,590 | 6/1989 | Tanabe et al. | 604/282 |
| 4,863,442 | 9/1989 | DeMello et al. | 604/282 |
| 4,898,591 | 2/1990 | Jang et al. | 604/282 |
| 5,017,259 | 5/1991 | Kohsai | 156/294 |
| 5,057,092 | 10/1991 | Webster, Jr. | 604/282 |
| 5,069,674 | 12/1991 | Fearnot et al. | 604/282 |
| 5,078,702 | 1/1992 | Pomeranz | 604/280 |
| 5,160,559 | 11/1992 | Scovil et al. | 156/73.6 |
| 5,190,520 | 3/1993 | Fenton, Jr. et al. | 604/43 |
| 5,217,440 | 6/1993 | Frassica | 604/282 |
| 5,221,270 | 6/1993 | Parker | 604/282 |
| 5,221,372 | 6/1993 | Olson | 148/326 |
| 5,234,416 | 8/1993 | Macaulay | 604/282 |
| 5,254,107 | 10/1993 | Soltesz | 604/282 |
| 5,279,596 | 1/1994 | Castaneda et al. | 604/282 |
| 5,306,252 | 4/1994 | Yuteri et al. | 604/164 |
| 5,335,305 | 8/1994 | Kosa et al. | 385/147 |
| 5,603,705 | 2/1997 | Berg | 604/282 |
| 5,769,796 | 6/1998 | Palermo et al. | 600/585 |

FOREIGN PATENT DOCUMENTS

| | | |
|---|---|---|
| 0 277 366 A1 | 8/1988 | European Pat. Off. . |
| 0 473 045 A1 | 3/1992 | European Pat. Off. . |

OTHER PUBLICATIONS

Kolobow et al., "A New Thin–Walled Nonkinking Catheter for Peripheral Vascular Cannulation", Surgery, vol. 68, No. 4, Oct., 1970, pp. 625–626.

*Primary Examiner*—Max Hindenburg
*Attorney, Agent, or Firm*—Crompton, Seager & Tufte, LLC

[57] ABSTRACT

A tubing assembly and method of manufacture for a catheter of the type having an inner tubular member defining a lumen, an outer tubular member surrounding said inner member, and a support member mounted between the tubular members to provide rigidity to the flexible catheter. The support member comprises a wire braid, and in the preferred embodiment comprises a stainless steel wire braid which has been tempered or hardened to give it a significantly high tensile strength. This higher tensile strength affords significantly greater kink resistance to the flexible catheter as the lumen size is increased and the wall thickness is decreased, however, the high tensile strength wire braid has the disadvantage of tending to flare out at its free ends. Therefore, means are provided for preventing the flaring of the wire braid during manufacture of the tubing assembly.

18 Claims, 4 Drawing Sheets

CATHETER HAVING AN ADHESIVE BRAID WIRE CONSTRAINT AND METHOD OF MANUFACTURE

CROSS REFERENCES TO CO-PENDING APPLICATIONS

This application is a continuation-in-part of U.S. patent application Ser. No. 08/441,260 filed Aug. 15, 1995, entitled "Catheter Joint with Restraining Device" now U.S. Pat. No. 5,603,705, which is a continuation of U.S. patent application Ser. No. 08/171,925, filed Dec. 22, 1993, entitled "Catheter Joint with Restraining Device" now abandoned, both of which are related to U.S. patent application Ser. No. 08/108,973, filed Aug. 18, 1993, entitled "Improved Thin-Walled Catheter", all assigned to the Assignee of this invention.

TECHNICAL FIELD

The present invention generally relates to the field of medical devices, and more particularly, to the field of catheters such as guide catheters used for the placement of medicines and medical devices within the body. Specifically, the invention is directed to a catheter tube, particularly useful in an intravascular guide catheter, incorporating an adhesive braid wire constraint.

BACKGROUND OF THE INVENTION

The use of intravascular catheters for treatment of the body is well known in the field of medicine. The need for a choice of catheter sizes and types has grown rapidly as the techniques for their use have been greatly improved and the types of medical uses have expanded quickly. One such catheter is a guide catheter which includes a tubular member having a lumen therethrough. Guide catheters are commonly used in diagnostic and treatment techniques related to vascular disease such as angioplasty. A guide catheter is inserted into the femoral artery and routed to a location near a treatment or diagnostic site through the aorta over the aortic arch to the ostium of a target vessel. The guide catheter provides a conduit so that fluid or another medical device can be delivered easily to the proximate location of treatment via the lumen of the guide catheter.

Prior art catheters often comprise a tubular member including a pair of congruent tubes, the inner one defining the lumen. A hub is connected at the proximal end of the tubes which in addition to providing access to the lumen for fluids and the like, is often used to provide torques and other necessary pressures to the tubes during their placement within the body. A tip of a selected design is placed at the distal end of the tubes. Flexibility is an essential part of the catheter so that it may be successfully torqued, pushed and pulled on its way through the vascular passage to the desired site in the body. For control of the catheter and to prevent its kinking from excessive flexing a certain amount of rigidity is also required. The prior art catheters often meet this need for rigidity by adding a support member between the two tubes. This support member may comprise a braid of metal wire wrapped around the inner tube, and often imbedded within the outer tube.

As specific examples of the type of prior art catheters described above, note U.S. Pat. No. 3,485,234, issued Dec. 23, 1969, to R. C. Stevens, for Tubular Products and Method of Making Same; and European Patent Application, Publication No. 0 277 366/A1, Priority Jun. 1, 1987, by Bruce H. Ward, for Guiding Catheter and Method for Making it. Each of these references teaches, in general, the prior art type of catheter discussed above.

One problem that has arisen is that as it becomes desirable to increase the diameter of the catheter lumen, it also becomes desirable to decrease the thickness of the walls of the tubes that form the catheter. However, it has been found that in thinner-walled catheters it is more difficult to prevent the kinking of the catheter. This negative effect on flexibility is overcome by the above cited co-pending Application, Ser. No. 08/108,973, filed Aug. 18, 1993, entitled "Improved Thin-Walled Catheter" which is incorporated by reference herein. The disadvantage of the prior art was overcome by providing a high tensile, stainless steel braid as the support structure. However, it has been found that the use of the high tensile metal braid may cause an additional problem for practitioners of the catheter art. It has been seen that the high tensile wire has a tendency to flare or spring out in an area proximate the ends of the braid both before and during the heating process used in joining the catheter to a tip or other apparatus. In a similar way, this flaring and springing of the support braid wire is found in prior art catheters even when using the lower tensile type of wire. This flaring will interfere in the proper joinder of the catheter to, for example, a tip and is clearly undesirable and unacceptable in an intravenous catheter.

It is recognized that guide catheters preferably have a low friction inner lumen for improved passage of other catheter devices, such as an angioplasty catheter, through such lumen. Catheters incorporating a lumen lined with polytetrafluoroethylene (PTFE) to insure low friction are generally known. The soft atraumatic tip of prior art catheters, however, does not incorporate a polytetrafluoroethylene liner. Due to the softness of the tip material and the absence of the PTFE liner, the tip area can add significant friction opposition to advancing devices through the inner lumen of the catheter. Further, it is recognized that extending the braid wire into the atraumatic tip is not desirable, as this would significantly stiffen the tip area and counter its function of providing an atraumatic positioning of the distal end of the guide catheter. Thus, it is the clinical function of the tip that requires such tip to be very soft and free of wire braid. Terminating the braid prior to the soft tip increases the prevalence of problems associated with the flaring or springing out of the wire braid proximate its free ends near the distal tip.

Accordingly, the need exists for a catheter tube construction incorporating a lubricous liner and overlying wire braid structure, wherein the free ends of the wire braid proximate the location of attachment of a soft atraumatic tip are prevented from flaring out during manufacture of the catheter tube. Further, a need exists for an atraumatic tip design which incorporates a lubricous liner to reduce the friction caused by the soft tip material when passing devices through the lumen of the tip. The present invention addresses these needs, as well as other problems associated with existing guide catheter tube and tip designs. The present invention also offers further advantages over the prior art and solves other problems associated therewith.

SUMMARY OF THE INVENTION

The present invention overcomes the above-identified disadvantages by providing an improved catheter tube incorporating a lubricous liner in combination with a wire braid overlying the lubricous liner, wherein the free ends of the wire braid are effectively restrained to overcome the inherent spring property of the material and prevent protrusion of the free ends proximal to the soft tip when assembled.

The present invention further provides a catheter tube incorporating a lubricous liner, preferably polytetrafluoroethylene, which extends at least through a portion of the inner lumen of the atraumatic tip to reduce friction therethrough. In a preferred embodiment, the liner extends through essentially the entire length of the inner lumen of the soft atraumatic tip.

The present invention further includes improved methods for joinder of the catheter to any selected apparatus, such as joinder of the tip to the catheter tube.

Two overall embodiments and methods of manufacturing these embodiments are disclosed herein. In a first embodiment, a lap-type joint is formed at the distal end of a section of catheter shaft subsequent to manufacture of a tubular member having an inner tube, an outer congruent tube and a wire braid therebetween. A means for restraining the free ends of the wire braid in the lap joint area is provided with subsequent addition of the atraumatic tip, a portion of which overlies the restrained free ends of the wire braid.

In a second embodiment, a braided shaft region and a non-braided tip region are formed over a continuous liner or inner tube, preferably a polytetrafluoroethylene liner or inner tube. This is achieved by sleeving a preformed segment of wire braid over a preformed inner tubular member or a liner. A molding sleeve is then tracked over the braid and inner tubular member which pulls the braid down tightly to the inner tubular member, including the flaring ends of the wire braid. With the molding sleeve in place, adhesive material is applied via capillary action to the region having the molding sleeve restraining the ends of the wire braid, which when cured hold the ends in place upon removal of the molding sleeve. This design further allows the inner tubular member to extend braid-free through a tip attached proximate the end of the wire braid.

In the preferred embodiment at least one end of the catheter, normally the distal end, is ground down by an abrasion tool to provide a length of reduced diameter suitable, in particular, for lap-joint type connection to a tip or other apparatus. A restraining material, preferably a thin-walled heat shrink polyester, is also provided to be placed over at least a portion of the reduced diameter length to prevent flaring of the metal braid during the joinder process.

In this embodiment, the restraining material can be in the form of a sleeve having a tubular shape with an inner diameter adapted to allow placement of the sleeve over at least a portion of the reduced diameter length at the end of the catheter; and a length at most equal to the length of the reduced diameter portion of the catheter.

As described, the apparatus and method of this embodiment provides the advantage of allowing use of the high tensile metal braid by restraining flaring of the metal during heat bonding to a tip or other device, thus improving kink performance in the thin-walled catheters which use the high tensile wire. The embodiment provides the same restraining advantage for catheters which may not use the high tensile wire, but which have the same flaring problem. This embodiment also provides the advantage of providing a more durable bond of the catheter to the tip or other apparatus by the increased surface area of the lap type bonding. Finally, the apparatus of this embodiment offers an additional advantage in the form of a stiffness transition in that the ground or abraded step portion of the bond balances the hardness of the main catheter to the softness of a tip, a balance which is known to provide clinical value.

In the second embodiment of the present invention, a catheter shaft construction is provided that incorporates adhesive means for preventing the free ends of a braid member from flaring outward during assembly. Further, this embodiment also provides a continuous inner tubular member or liner that is preferably lubricous, such as polytetrafluoroethylene, which extends through the tip portion of the catheter tubular member, yet has a portion which is free of the braid member. With the inner liner extending through the catheter shaft and tip, the braid or braid wire ends uniformly just proximal to the beginning of the distal soft tip, which results in the above-identified flaring of the braid wire. Thus, a preferred method has been developed to restrain the flaring braid wires during assembly of the catheter shaft which provides for a continuous liner for both the shaft and tip regions and a braid-free tip section. The method does not require braid removal and does not add wall thickness to restrain the flared ends.

With this second preferred embodiment, a first step in the method of manufacture is to form a braided shaft region and a non-braided tip region over a continuous liner. This is preferably achieved by sleeving the braid or wire braid over a section of liner which is placed over a core or mandrel. The distal end of the braid terminates proximal to the distal end of the liner to separate the shaft and tip regions.

A molding sleeve is then tracked over the braid and liner. The molding sleeve is preferably a tubular member having a lumen therethrough which, when tracked over the braid, pulls the braid wire down tightly to conform to the outer longitudinal surface of the liner. At the end of the wire braid, the advancing molding sleeve forces the free braid ends to conform back into the original braid pattern and into the lumen of the molding sleeve. Once the distal ends of the braid member have been conformed by the molding sleeve, adhesive means is injected into the cavity between the molding sleeve and the liner over a portion of the braid proximate its distal end. Preferably a high temperature (350–400° F.), soft (25D–50D) restraining seal in liquid form is injected into the cavity. Capillary action is recognized as facilitating this process by sucking the liquid seal restraining material from outside the molding sleeve to inside.

The liquid seal is then cured through the molding sleeve. A preferred adhesive means is an ultraviolet light (UV) curable adhesive which is used in conjunction with a clear molding sleeve that allows UV light to pass through the clear molding sleeve walls which cures the adhesive. Although other adhesives and curing methods and appropriate adhesives are recognized as within the scope of the invention, including such methods as heat, catalyst and moisture.

Upon removing the molding sleeve, the resulting intermediate assembly or tubular assembly includes a micro-thin band molded from the adhesive means or liquid seal that circumferentially encapsulates the distal free wire ends. The restraining band preferably adheres to the liner and encapsulates the wire braid. The band is very thin, uniform in thickness, and concentric, due to the forming of the liquid seal within the molding sleeve. The wire braid ends are uniformly and distinctly ended while the inner tubular member or liner continues distally to provide a braid-free region for tip attachment.

An outer tubular member overlies the intermediate tube assembly over at least a portion of the assembly having the braid thereon. A tip member overlies the portion of the liner which extends distally beyond the braid. The distal end of the tip member can extend beyond the distal end of the liner, but in preferred embodiments, the tip member is co-extensive with the liner to provide an atraumatic tip having a continuous liner therethrough.

These and other various advantages and features of novelty which characterize the present invention are pointed out with particularity in the claims annexed hereto and forming a part hereof. However, for a better understanding of the invention, its advantages and the objects obtained by its use, reference should be made to the drawings which form a further part hereof and to the accompanying descriptive matter, in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF PREFERRED EMBODIMENTS

Figure 1:
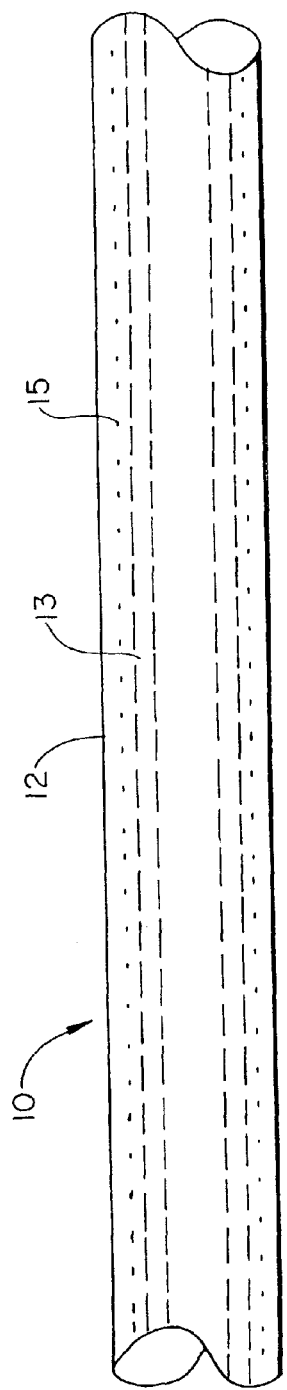
FIG. 1 is a plan view showing a portion of a catheter.
Figure 2:
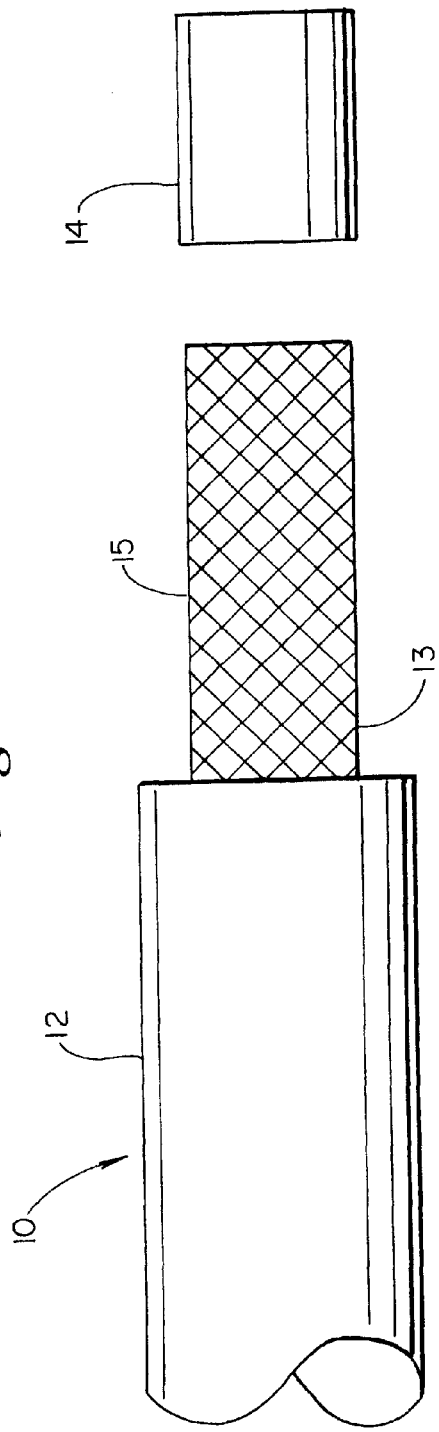
FIG. 2 is another plan view of a portion of the catheter of FIG. 1 with a length of the catheter ground down to a lesser diameter, and showing a sleeve.
Figure 3:
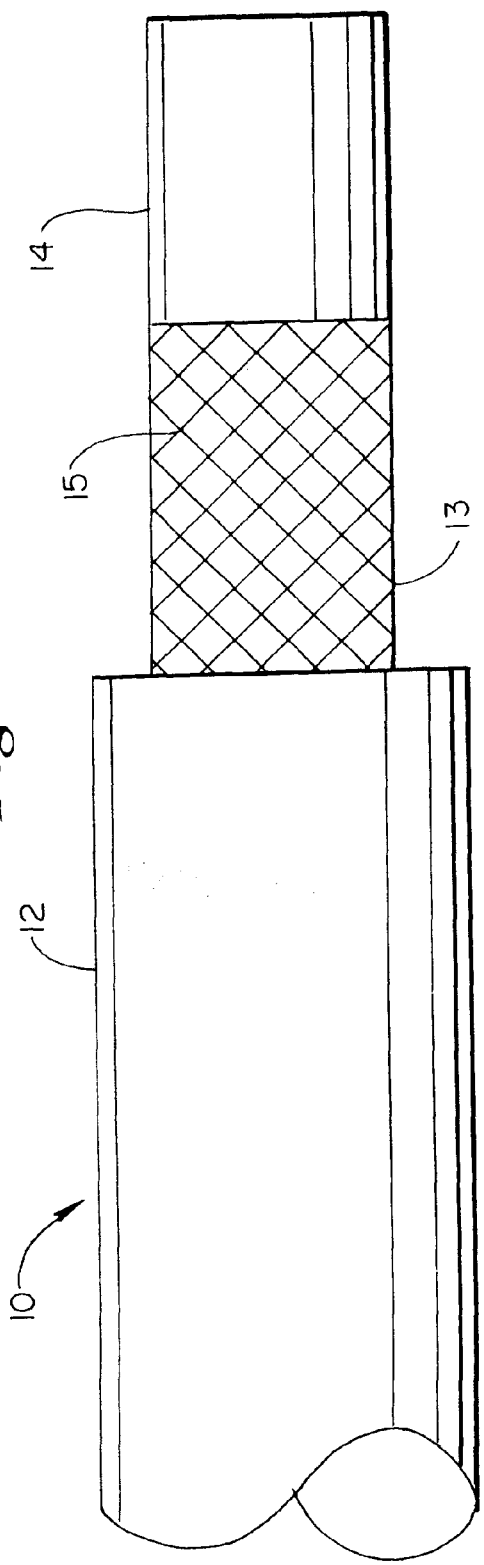
FIG. 3 is a plan view of FIG. 2 showing the sleeve after mounting on the ground-down length of the catheter.

As required, detailed embodiments of the present invention are disclosed herein. However, it should be understood that the disclosed embodiments are merely exemplary of the present invention which may be embodied in various systems. Thus, the discussion with respect to FIGS. 1–3 are directed to a first embodiment of the present invention, while the discussion with respect to FIGS. 4–8 are directed to a second embodiment. It is, however, recognized that elements of each embodiment may be incorporated in a catheter tube construction in combinations as would be well understood by one skilled in the art. Therefore, specific details disclosed herein are not to be interpreted as limiting, but rather as a basis for the claims and as a representative basis for teaching one skilled in the art to variously practice the present invention.

FIG. 1 shows a guide catheter 10, which may be a thin-walled catheter. Catheter 10 comprises an outer tubular member 12 which surrounds and is coaxial with an inner tubular member 13 shown in dashed phantom lines. A support member 15 is shown in dotted phantom lines. Member 15 is a braid of metal wire, which may be high tensile wire, that also surrounds and is coaxial with member 13.

FIG. 2 is a drawing of a portion of catheter 10. Member 12 is shown having an end portion ground or abraded away.

As shown in FIG. 2, member 12 has been completely ground down to metal braid 15. However, it should be recognized that this invention will also operate fully if only a portion of member 12 is abraded away. FIG. 2 also shows a restraining device 14. Device 14 is shown in a first preferred embodiment to be a tubular sleeve. Sleeve 14 is, preferably, a thin-walled heat shrink polyester having a length sized to cover at least a portion of the abraded length of member 12, and an inner diameter sized to allow it to fit over the reduced diameter of the end portion of catheter 10 caused by the abrasion of member 12. In this preferred embodiment, sleeve 14 has a thickness of approximately 0.0005 inches, thus allowing it to be completely imbedded between the reduced diameter portion of catheter 10 and the tip or other device used to complete the lap joint with catheter 10.

FIG. 3 is a plan view of the apparatus of FIG. 2 showing the restraining device 14 mounted on the reduced diameter portion of catheter 10. Due to the proper sizing of device or sleeve 14, it has been slid onto and covers at least a portion of the reduced diameter region of catheter 10. Sleeve 14 is seen to fit over enough of the end portion of braid 15 so that, when sleeve 14 is heated, it will shrink to and retain the metal wire strands of braid 15.

It should be recognized that though restraining device 14 is shown and described as a tubular member in this embodiment, other forms could be used as well. For example, device 14 could be a simple strip of heat shrink polyester adapted to be wrapped around the reduced diameter portion of catheter 10. The important feature is that after it has been heated to encapsulate the end of the wire braid, device 14 restrains the wire from surfacing through any joinder by flaring or springing out.

For the process of forming the apparatus of this invention, an abrasive forming tool is used to remove the material of member 12 from its outside surface for 360 degrees from one end of catheter 10. This forms a straight step from the end which allows the abraded or ground portion of catheter 10 to act as the male portion of a lap joint to coact with a female portion of a soft tip or other device it is desired to connect to the apparatus of this invention. The step is preferably a reduction in wall thickness of approximately 0.002 to 0.006 inches, thus allowing for the use of the 0.0005 inch restraining device 14. The length of the abraded portion of catheter 10 is preferably about 0.125 inches, thus allowing for a significant bonding surface area when used in a lap joint. As used herein, the terms "ground" and "abraded" have the same meaning.

Figure 6:
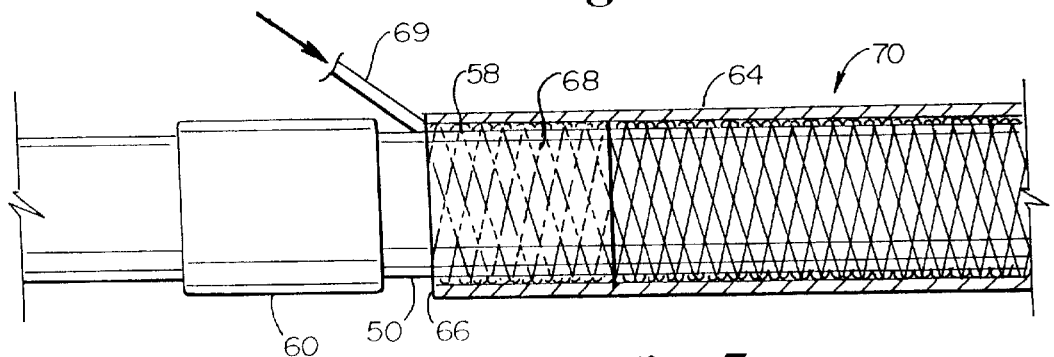
FIG. 6 is a partial cross-sectional view illustrating addition of adhesive means to the distal portion of the assembly between the liner and molding sleeve.
Figure 7:
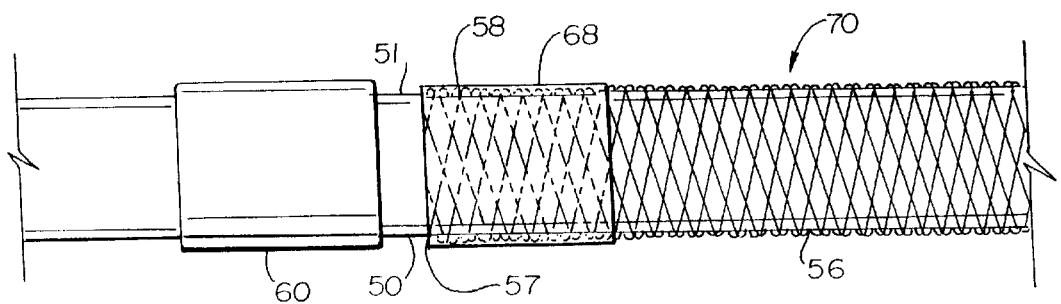
FIG. 7 is a plan view illustrating the restrained braid ends upon curing of the adhesive means and removal of the molding sleeve.
Figure 8:
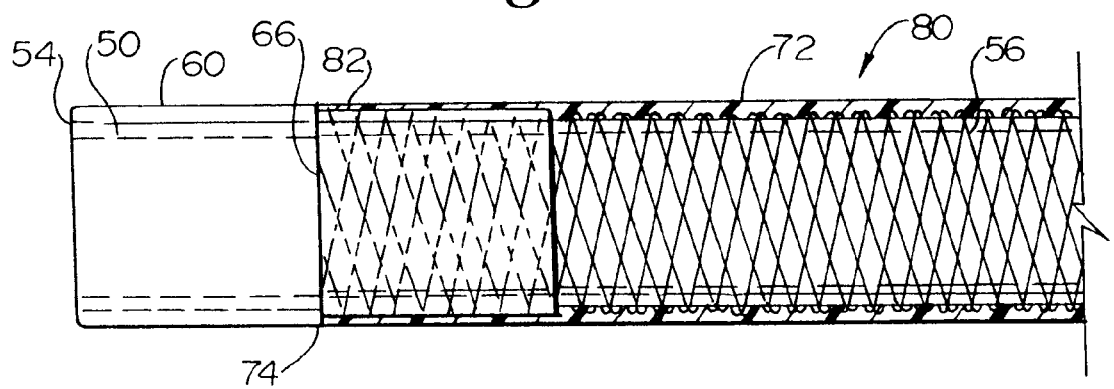
FIG. 8 depicts a partial cross-section of a distal portion of a catheter shaft of the embodiment of FIG. 7 with an outer tubular member overlying the braid assembly and a tip portion overlying the liner distal of the braid assembly.

Now referring to FIGS. 4–8, a series of illustrations are provided to depict and describe another preferred embodiment of the catheter tubular assembly of the present invention and a method of manufacturing such tubular assembly. The method of manufacture of the final tubular assembly depicted in FIG. 7 and the catheter assembly depicted in FIG. 8 is first described for a better understanding of the final apparatus.

Figure 4:
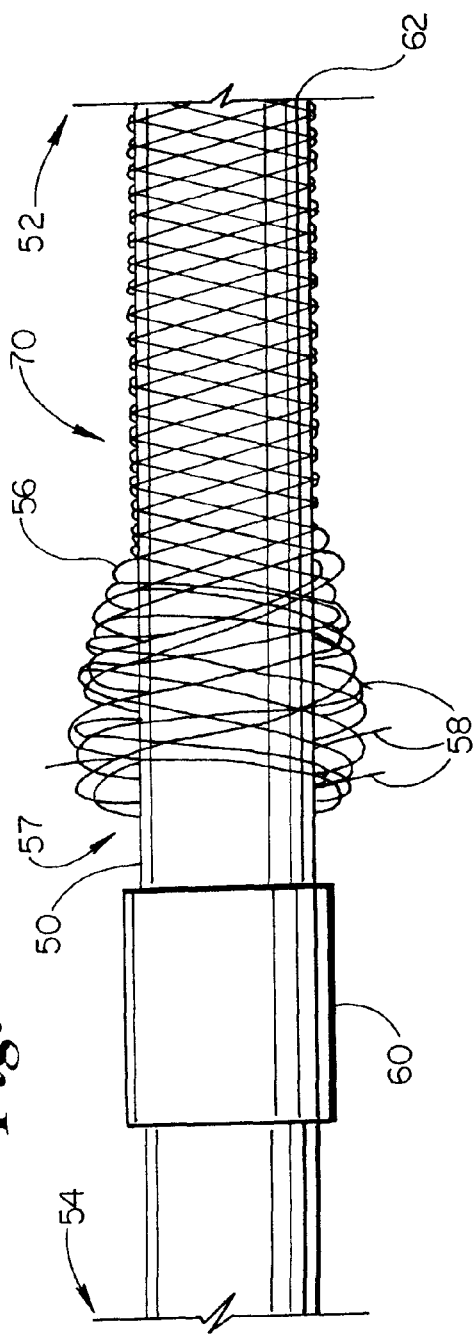
FIG. 4 is a plan view of a liner or inner tubular member having a braid member inserted thereover illustrating the flared free ends of the braid.

Referring now to FIG. 4, a tubular member 50 is first provided for manufacture of a tubular assembly 70 of the present invention. The tubular member 50 preferably has a lumen 62 therethrough. However, during manufacture of the tubular assembly, a mandrel or core is inserted in the lumen 62 to prevent collapse of the tubular member 50. The mandrel can include a stainless steel wire or a polymeric rod.

The tubular member 50 is preferably manufactured from a lubricous polymeric material. A preferred material of construction is polytetrafluoroethylene (PTFE). In the preferred method of manufacture, the tubular member 50 is cut to a discrete length slightly in excess of the length of a desired finished product. A braided wire tubular member 56 overlies a portion of the outside longitudinal surface 51 over a portion of the length of the tubular member 50. The braid 56 is preferably manufactured from metallic wire. A preferred material of construction is stainless steel, more preferably a high tensile stainless steel wire. In a preferred method of manufacture, the braid 56 is preformed into a braided wire tubular member 56 of required length which is sleeved over the tubular member 50.

As depicted in FIG. 4, the braid 56 has a distal end shown generally at 57. The distal end 57 flares outward due to the inherent spring property of the stainless steel material which is utilized in a preferred embodiment. The distal free ends 58 pose problems in assembly of catheter tubing as described previously.

Also depicted in FIG. 4 is a tip member 60 which has been preloaded onto the tubular member 50 by sliding the tip member over the distal end 54 of the tubular member 50. The final assembly of the tip member 60 to the catheter shaft will be described later in conjunction with FIGS. 7 and 8.

Figure 5:
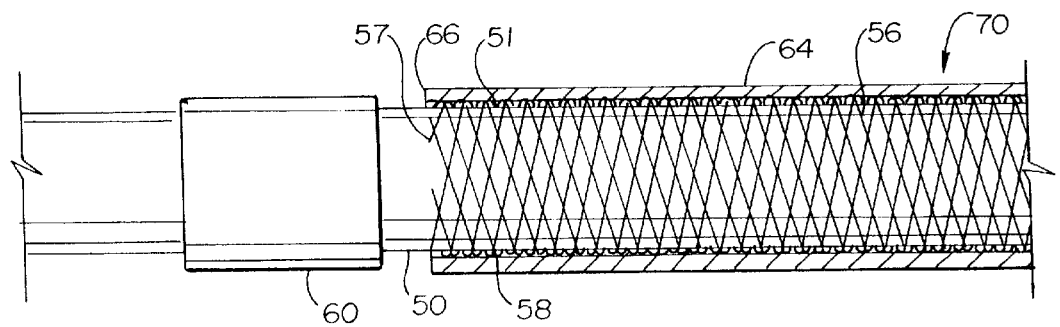
FIG. 5 is a partial cross-sectional view of the assembly of FIG. 4 having a molding sleeve inserted thereover to conform the wire braid.

Now referring to FIG. 5, the assembly of FIG. 4 is depicted having a molding sleeve 64 disposed thereover. The molding sleeve has a distal end 66 and a proximal end 67 (not shown). As depicted in FIG. 5, the molding sleeve 64 includes a tubular portion having a lumen therethrough. The molding sleeve 64 is tracked over the tubular member 50 and braid 56 so that the braid 56, including the free ends 58, are caused to conform to the outside longitudinal surface 51 of the tubular member 50. FIG. 5 depicts a preferred embodiment, wherein the distal end 66 of the molding sleeve 64 terminates proximate the distal end 57 of the braid 56.

With the molding sleeve 64 positioned as depicted in FIG. 5, now referring to FIG. 6, adhesive means 68 is applied to the tubular member 50 proximate the restrained free ends 58 under the molding sleeve 64 to prevent flaring of the free ends 58 upon removal of the molding sleeve 64. In preferred embodiments, the adhesive means 58 is simply applied by depositing a bead of adhesive through a syringe or other applicator 69 around the circumference of the tubular member 50 at the distal end 66 of the molding sleeve 64. Capillary action assists in drawing the adhesive means 58 under the distal end 66 of the molding sleeve 64 between the tubular member 50, longitudinal surface 51 and molding sleeve 64.

In preferred embodiments, the adhesive means 58 is an ultraviolet light curable adhesive. These adhesives can include: polyurethanes, epoxies, acrylics and mixtures thereof. However, it is recognized that other adhesives which are heat curable, catalyst curable or moisture curable can be utilized. These other adhesives can include: cyanoacrylates, epoxies, hot melt adhesives, acrylics, silicones and mixtures thereof.

Upon application of the adhesive means 68, the adhesive means 68 is cured while the molding sleeve 64 remains in place. In a preferred embodiment, wherein the adhesive means 68 is ultraviolet light curable, the molding sleeve 64 must allow passage of ultraviolet light through the walls thereof. Therefore, the molding sleeve is preferably clear. The clear molding sleeve 64 also allows visualization of the braid 56 as it is conformed to the tubular member 50.

Now referring to FIG. 7, the finished tubular assembly 70 or intermediate assembly 70 for use in manufacturing a catheter is illustrated. As shown, upon curing of the adhesive means 68, the molding sleeve 64 is removed and the adhesive means 68 restrains the free ends 58 of the braid 56.

As depicted in FIG. 7, the thickness of the adhesive means 68 is grossly exaggerated so that it is visible. In preferred embodiments, the adhesive means 68 provides a uniform, micro-thin seal which is molded circumferentially around the distal braid ends 58. The thickness of the adhesive means 68 does not interfere with subsequent processing of the tubular assembly 70.

Thus, the tubular assembly 70 of the present invention includes a tubular member 50 having a proximal end, a distal end and an outer longitudinal surface 51. The braid member 56 overlies the tubular member 50 and conforms to the outer longitudinal surface 51. The braid 56 has a distal end 57 which includes a plurality of free ends or terminal ends 58. A sufficient quantify of adhesive means 68 restrains the plurality of terminal ends 58 of the braid member 56 to maintain conformance of the plurality of terminal ends 58 to the longitudinal surface 51 of the tubular member 50.

The tubular assembly of FIG. 7 is preferably incorporated into a catheter assembly 80 as depicted in FIG. 8. As depicted in FIG. 8, an outer tubular member 72 overlies the braid member 56 and has a distal end 82 terminating proximate the distal end 66 of the braid member 56. The outer tubular member 72, however, terminates proximal of the distal end 54 of the inner tubular member 50.

The tip member 60, previously disclosed, includes at least a portion of the tip member 60 overlying the inner tubular member 50 outer longitudinal surface 51 distal of the distal end 66 of the braid member 56. As depicted in FIG. 8, the proximal end 74 of the tip member 60 is in contact with the distal end 82 of the outer tubular member 72. As depicted in a preferred embodiment, the inner tubular member 50 distal of the braid member 56 is co-extensive with the tip member and forms a braidless tip portion of the catheter assembly 80 having a continuous inner tubular member therethrough.

It is recognized that the outer tubular member 72 may be added in any way known in the art. This can include extruding a material over the tubular assembly 70. In a preferred method of manufacture, a plurality of tubular segments are slidably received over the tubular assembly 70 along with the tip member 60. The tubular members, including the tip member 60, are abutted to each other and a heat shrink polymer sleeve is placed over the entire assembly. The assembly is then heated or baked to fuse the assembly with subsequent removal of the polymer sleeve. This preferred method of manufacture is disclosed in detail in co-pending, commonly assigned, application Ser. No. 08/800,927, now 58/1715 filed on the same date as the present application, entitled "Catheter Having Flexural Modulus Designs to Curved Shapes", the disclosure of which is incorporated herein by reference.

Having thus described the preferred embodiments of the present invention, those of skill in the art will readily appreciate the other useful embodiments within the scope of the attached claims.

What is claimed is:

1. A tubular assembly for use in catheter construction comprising:

a. a tubular member having a proximal end, a distal end and an outer surface;

b. a braid member including a plurality of metallic filaments overlying said tubular member conforming to said outer surface, said braid member further including a plurality of terminal ends defined by ends of said metallic filaments proximate the distal end of said tubular member; and c. a sufficient quantity of adhesive means restraining said plurality of terminal ends of said braid member to maintain conformance to said outer surface, said adhesive means forming a band that extends circumferentially around the tubular member and encapsulates the terminal ends of said metallic filaments.

2. The tubular assembly of claim 1, wherein said braid member comprises a metallic braided wire assembly.

3. The tubular assembly of claim 2, wherein said metallic braided wire is high tensile stainless steel.

4. The tubular assembly of claim 1, wherein said tubular member is manufactured from a lubricous polymeric material.

5. The tubular assembly of claim 4, wherein said lubricous material is polytetrafluoroethylene.

6. The tubular assembly of claim 1, wherein said adhesive means is an ultraviolet light curable adhesive.

7. The tubular assembly of claim 6, wherein said ultraviolet light curable adhesive is selected from the group consisting of: polyurethanes, epoxies, acrylics and mixtures thereof.

8. The tubular assembly of claim 1, wherein the adhesive means is an adhesive selected from the group consisting of: cyanoacrylates, epoxies, hot melt adhesives, acrylics, silicones and mixtures thereof.

9. A catheter assembly comprising:
   a. an inner tubular member having a proximal end, a distal end, an outer surface and a lumen therethrough;
   b. a braid member including a plurality of metallic filaments overlying said inner tubular member outer surface and conforming thereto, said braid member further having a distal end, wherein said braid member distal end is defined by a plurality of terminal ends of said metallic filaments, said distal end terminating proximal of said distal end of said inner tubular member;
   c. an outer tubular member overlying said braid member having a distal end terminating proximate said distal end of said braid member proximal to said distal end of said inner tubular member;
   d. adhesive means restraining said plurality of terminal ends of said braid member to maintain conformance to said outer surface, said adhesive means forming a band that extends circumferentially around the tubular member and encapsulates the terminal ends of said metallic filaments; and,
   e. a tip member having a lumen therethrough, at least a portion of said tip member overlying said inner tubular member outer surface distal of said distal end of said braid member, wherein said tip member has a proximal end in contact with said distal end of said outer tubular member.

10. The catheter assembly of claim 9, wherein said inner tubular member extends through the entire length of said tip member.

11. The catheter assembly of claim 9, wherein said tip member and said portion of said inner tubular member distal of said braid member are coextensive, forming a braidless tip portion of said catheter assembly having a continuous inner tubular member therethrough.

12. The catheter assembly of claim 9, wherein said braid member comprises a metallic braided wire assembly.

13. The catheter assembly of claim 12, wherein said metallic braided wire is high tensile stainless steel.

14. The catheter assembly of claim 9, wherein said tubular member is manufactured from a lubricous polymeric material.

15. The catheter assembly of claim 14, wherein said lubricous material is polytetrafluoroethylene.

16. The catheter assembly of claim 9, wherein said adhesive means is an ultraviolet light curable adhesive.

17. The catheter assembly of claim 16, wherein said ultraviolet light curable adhesive is selected from the group consisting of: polyurethanes, epoxies, acrylics and mixtures thereof.

18. The catheter assembly of claim 9, wherein the adhesive means is an adhesive selected from the group consisting of: cyanoacrylates, epoxies, hot melt adhesives, acrylics, silicones and mixtures thereof.

\* \* \* \* \*